United States Patent [19]

Spector

[11] Patent Number: 4,858,831
[45] Date of Patent: Aug. 22, 1989

[54] HAND-ACTUATED FRAGRANCE EMITTING UNIT

[76] Inventor: Donald Spector, 380 Mountain Rd., Union City, N.J. 07087

[21] Appl. No.: 158,835

[22] Filed: Feb. 22, 1988

[51] Int. Cl.$^4$ .............................................. B05B 11/04
[52] U.S. Cl. .................................... 239/326; 239/56; 239/327
[58] Field of Search ................. 239/34, 326, 327, 328, 239/36, 53–56

[56] References Cited

U.S. PATENT DOCUMENTS

| | | | |
|---|---|---|---|
| 2,179,871 | 11/1939 | Vogel | 239/326 |
| 2,239,716 | 4/1941 | Hothersall | 239/326 |
| 2,348,420 | 5/1944 | Rose | 239/326 |
| 2,618,892 | 11/1952 | Locks et al. | 239/53 |
| 2,625,432 | 1/1953 | Tupper | 239/327 |
| 2,786,717 | 3/1957 | Rausch | 239/327 |
| 3,162,371 | 12/1964 | Palmer et al. | 239/327 |
| 3,382,871 | 5/1968 | Parry | 239/326 |
| 3,412,907 | 11/1968 | Faso | 239/56 |
| 4,465,232 | 8/1984 | Field | 239/36 |
| 4,723,691 | 2/1988 | Minkevitch et al. | 239/327 |

FOREIGN PATENT DOCUMENTS 568910  7/1958  Belgium .............................. 239/327

Primary Examiner—Andres Kashnikow
Assistant Examiner—Michael J. Forman
Attorney, Agent, or Firm—Michael Ebert

[57] ABSTRACT

A fragrance emitting unit which when hand actuated expels into the atmosphere a pulse of fragrance. Included in the unit is an air-filled container provided with a small jet opening, the container having a flexible wall which when depressed subjects the air in the container to pressure to cause a pulse of air to be expelled through the opening. Interposed between the jet opening and the interior of the container is an air-permeable, porous member impregnated with liquid fragrance whereby when the unit is first actuated, a pulse of air is forced through the member to extract fragrance therefrom to produce a fragrance mist that is discharged through the opening. When the wall is then released and seeks to resume its normal state, the resultant vacuum created within the container causes air to be drawn into the jet opening and to be forced through the member into the interior so that the charge of air in the container is now laden with fragrance. As a consequence, when the unit is again actuated, the mist expelled therefrom carries a high concentration of fragrance.

8 Claims, 1 Drawing Sheet

U.S. Patent
Aug. 22, 1989
4,858,831
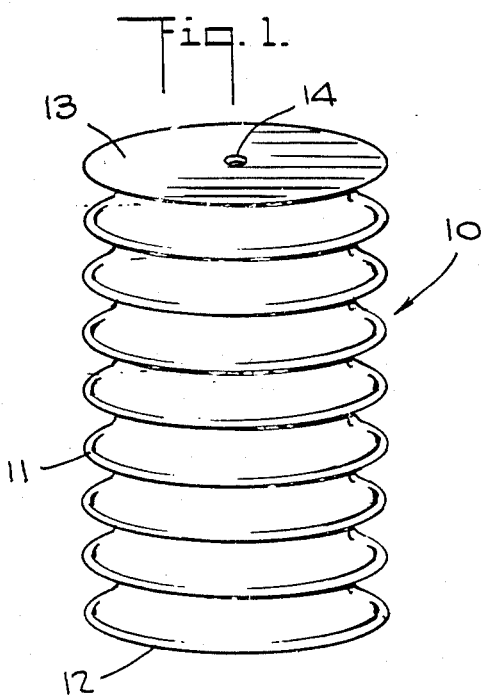
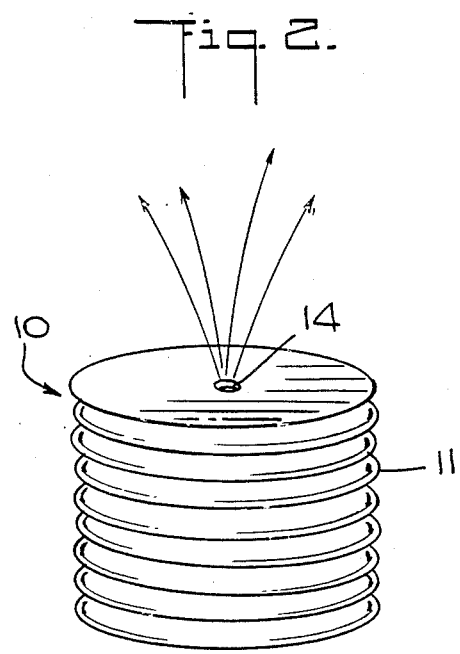
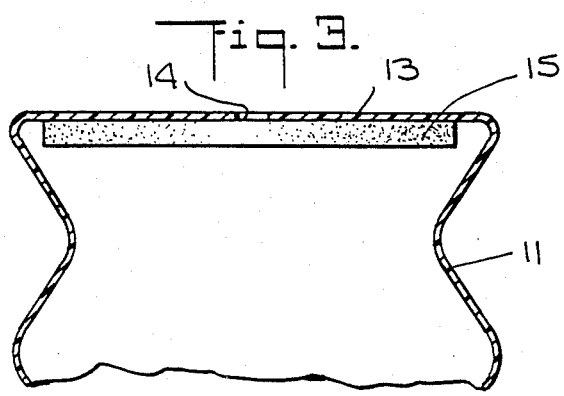
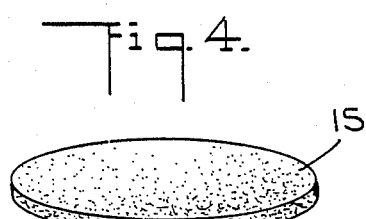
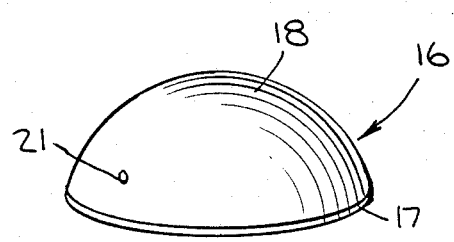
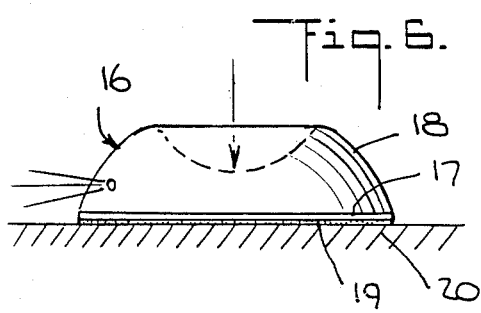
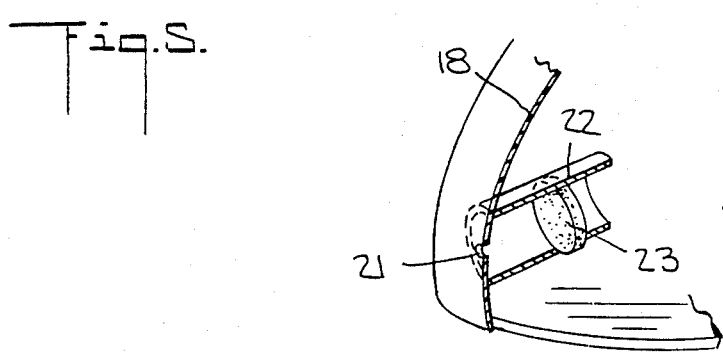

HAND-ACTUATED FRAGRANCE EMITTING UNIT

BACKGROUND OF INVENTION

1. Field of Invention:

This invention relates generally to aroma generators functioning to exude a fragrance into a room, and more particularly to a hand-actuated fragrance emitting unit which when manually actuated expels into the atmosphere a fragrance mist.

2. Status of Prior Art:

As used herein, the term "aroma" or "fragrance" is not limited to pleasant or savory smells but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

There are many situations in which the environment of a living room, a kitchen, an office or other enclosure occupied by people is rendered unpleasant by tobacco smoke, food smells or other pungent odors. It is often not practical, as in the winter months, to open a window or operate an air conditioner to clear the air. The common practice, therefore, is to mask or modify the prevailing atmosphere by some sort of air freshener device or aroma generator.

In some situations, the atmosphere of a room may be clear and free of odors, yet it may be desirable to introduce a fragrance in order to create a more romantic ambience or to induce other effects, for personal moods are highly influenced by odors. Thus, the effect of a musk-like odor is very different from that of sea air and such differences can be exploited when manipulating the environment.

It is known to provide an air freshener or fragrance generator in the form of a bottle containing a volatile liquid in which a wick is immersed, the upper end of the wick extending above the bottle and being exposed to the air. Such devices not only are subject to spillage or leakage, but, in order to adjust the rate of volatilization, means must be provided to vary the extent of wick exposure.

The Meek U.S. Pat. No. 2,763,395, discloses an air freshener in which a vented cylindrical container is filled with particles of absorbent material impregnated with a volatile air-freshener liquid. The vented container is telescoped within a cylindrical housing and is provided with detents making it possible to more or less raise the vented container relative to its housing and thereby more or less expose the impregnated particles to the atmosphere. In this way, one can adjust the rate of odor or air freshener dissemination. A vapor dispenser having telescoping elements to adjust the rate of dissemination is also shown in the Martens et al. U.S. Pat. No. 4,220,281.

In the Munnecke U.S. Pat. No. 2,578,827, a deodorized unit is disclosed in which an absorbent filler held in a container is impregnated with a volatile liquid. In this unit the rate of emission is controlled by an adjustable shutter in which two sets of holes are more or less brought into registration with each other.

Also of background interest is my prior U.S. Pat. No. 4,612,223 in which fragrance-emitting pellets are housed in a box having openings therein to discharge the fragrance emitted from the pellets into the atmosphere.

The disadvantage of aroma generators in which the fragrance is stored in a porous member is that the fragrance is slow to volatilize. While it is possible to provide a motor driven propeller to force air through the porous member and thereby increase the emission of fragrance, such devices require power; hence, it is necessary to provide batteries or a power outlet plug-in arrangement, thereby adding substantially to the cost of the generator. It is also possible to increase evaporation of a fragrance compound beyond its ambient capacity by heaters, but this, too, complicates the unit.

SUMMARY OF INVENTION

In view of the foregoing, the main object of this invention is to provide a hand-actuated fragrance emitting unit which when actuated forces a pulse of air through a porous member saturated with fragrance to produce a mist of fragrance.

A significant advantage of the invention is that it makes possible to quickly change the atmosphere of a room by repeatedly actuating the unit to produce a succession of discharges.

More particularly, an object of this invention is to provide a disposable unit of exceptional simplicity and low cost, the unit including a container having a flexible wall which when depressed produces pressurized air that is forced through a fragrance-saturated porous member.

Briefly stated, these objects are attained in a fragrance emitting unit which when hand actuated expels into the atmosphere a pulse of fragrance. Included in the unit is an air-filled container provided with a small jet opening, the container having a flexible wall which when depressed subjects the air in the container to pressure to cause a pulse of air to be expelled through the opening. Interposed between the jet opening and the interior of the container is an air-permeable, porous member impregnated with liquid fragrance whereby when the unit is first actuated, a pulse of air is forced through the member to extract fragrance therefrom to produce a fragrance mist that is discharged through the opening. When the wall is then released and seeks to resume its normal state, the resultant vacuum created within the container causes air to be drawn into the jet opening and to be forced through the member into the interior so that the charge of air in the container is now laden with fragrance. As a consequence, when the unit is again actuated, the mist expelled therefrom carries a high concentration of fragrance.

BRIEF DESCRIPTION OF DRAWINGS

For a better understanding of the invention as well as other objects and further features thereof, reference is made to the following detailed description to be read in conjunction with the accompanying drawings, wherein:

FIG. 1 is a perspective view of a first embodiment of a hand-actuated unit in accordance with the invention;

FIG. 2 shows the unit when it is actuated to emit a fragrance mist;

FIG. 3 is a section taken through the unit to show the fragrance pad;

FIG. 4 is a separate view of the pad;

FIG. 5 shows in perspective another embodiment of a unit in accordance with the invention;

FIG. 6 shows the unit attached to a wall in its actuated state; and

FIG. 7 is a section taken through the unit showing the fragrance disc housed therein.

DESCRIPTION OF INVENTION

First Embodiment:

Referring now to FIGS. 1 to 4, there is shown a hand actuated fragrance emitting unit constituted by a blow-molded container 10 formed of flexible synthetic plastic material such as polyvinyl chloride or polyethylene. Container 10 is provided with a cylindrical wall 11 in a bellows or accordian-like formation, the lower end of the cylinder being enclosed by a disc-shaped, relatively rigid base 12, and the upper end by a disc-shaped, relatively rigid top 13. Formed in the center of top 13 is a small jet opening 14.

Supported directly under top wall 13 is a disc-shaped pad 15 of air-permeable, porous material fabricated of paper, cotton, non-woven fabric or other highly absorbent material. Pad 15 is saturated with a liquid fragrance whose aroma is appropriate to the use to which the unit is put.

In order to either enhance or restrict the volatility of the liquid fragrance so as to obtain satisfactory perception of the fragrance over a predetermined span of time, one can either increase or reduce the vapor pressure of the fragrance compound. Ethyl alcohol will increase vapor pressure, thereby increasing perception of the fragrance while reducing its perceptive life. However, by adding dibutylpthalate to the liquid fragrance, this substance will reduce the perception of the fragrance and hence increase its life.

In practice, the pad may be formed of "Interflo" porous plastic which is molded of pure, ultra high molecular weight polyethylene with a controllable pore structure. The advantage of "Interflo" plastic is that it is inert to fragrance compounds and will therefore release a true fragrance.

When the container 11 is manually pressed down, as shown in FIG. 2, this acts to compress the bellows, thereby subjecting the air in the container to pressure to force the air through pad 15 for discharge from opening 14. The entire pad, whose underside is exposed to the air-filled interior of the container, is subjected to air pressure. The pressurized air forced through the pad extracts fragrance therefrom, so that the pulse of air emitted from the jet opening is laden with fragrance.

When container 14 is thereafter released, it resumes its normal shape, as shown in FIG. 1, and in doing so, it creates a vacuum in the container, thereby causing air to be drawn into opening 14 and through pad 15 into the interior. The incoming air therefore picks up fragrance from the pad, so that the interior of the container is now filled with fragrance laden air.

The next time the unit is actuated, the air forced through the pad is already laden with fragrance and picks up more fragrance, so that now the emitted pulse is much richer in fragrance. Thus, even when the unit is inactive for a prolonged period, when it is again actuated, a concentrated fragrance mist will be discharged into the atmosphere.

Second Embodiment:

In the embodiment shown in FIGS. 5 to 7, container 16 is provided with a relatively rigid, circular plastic base 17 having a hollow dome 18 formed of flexible plastic material integral with the base. A layer 19 of pressure-sensitive material is secured to the undersurface of the base, so that this unit may be attached to any wall surface 20, such as a bathroom tile or the dashboard of an automobile.

Formed in dome 18 adjacent base 17 is a jet opening 21. Mounted in close proximity to jet opening 21 in the interior of dome 18 by means of a short tube 22 is a porous, air permeable disc 23 of ceramic or other suitable absorbent or adsorbent material impregnated with a liquid fragrance. Tube 22 is sealed at one end to dome 18 to surround opening 21 so that in order for air to pass from the interior of the dome into the atmosphere through opening 21, it must first go through disc 23. In practice, the dome may be in a corrugated formation defined by circular rings of progressively greater diameter as one goes from the top to the bottom of the dome.

The operation of this unit is the same as in the first embodiment; for when dome 18 is pressed down, as shown in FIG. 6, the resultant air pressure produces a pulse of air that is forced through disc 23 to pick up liquid fragrance which is discharged as a mist through opening 21 into the atmosphere.

While there has been shown and described a preferred embodiment of a hand-activated fragrance emitting unit in accordance with the invention, it will be appreciated that many changes and modifications may be made therein without, however, departing from the essential spirit thereof. Thus, the container may take the form of a squeeze bottle formed of flexible plastic material having a small opening or an array of small openings at its upper end. While there is very little leakage from the small opening, in practice this may be covered by a removable cap.

I claim:

1. A hand actuated fragrance emitting unit comprising:
   (A) an air-filled container free of liquid which is sealed except for a small jet opening, said container having a flexible wall which when manually depressed repeatedly by a user subjects air in the interior of the container to pressure to cause pulses of air to be expelled from the opening; and
   (B) an air-permeable, porous, disc-shaped member interposed between the jet opening and the interior of the container, the entire inner surface of the member being exposed to the air in the container, said member being impregnated with a volatile liquid fragrance whereby when the wall is depressed, a pulse of pressurized air is forced through the member to extract liquid fragrance therefrom to produce a fragrance pulse that is discharged as a mist through the opening, the wall when released resuming its normal shape and in doing so creating a vacuum in the container causing air to be drawn into the jet opening and through the member so that the container air is now laden with fragrance.

2. A unit as set forth in claim 1, wherein said member is formed by a porous polyethylene material.

3. A unit as set forth in claim 1, wherein said member is formed of absorbent paper.

4. A unit as set forth in claim 1, wherein said container has a flexible cylindrical wall in an accordian formation enclosed at either end, one end having said opening therein.

5. A unit as set forth in claim 1, wherein said container is formed by a circular base and a hollow dome integral therewith formed of flexible plastic material.

6. A unit as set forth in claim 5, wherein said opening is in said dome adjacent said base.

7. A unit as set forth in claim 5, wherein said base is provided at its undersurface with a pressure-sensitive adhesive layer.

8. A unit as set forth in claim 1, wherein said fragrance is a volatile perfume.

* * * * *